(12) United States Patent
Zong et al.

(10) Patent No.: US 12,406,765 B2
(45) Date of Patent: Sep. 2, 2025

(54) INTELLIGENT SYSTEM FOR SEARCH AND RESCUE IN SPECIAL ENVIRONMENT SUCH AS DISASTER

(71) Applicant: Army Medical University, Chongqing (CN)

(72) Inventors: Zhaowen Zong, Chongqing (CN); Wenqiong Du, Chongqing (CN); Xin Zhong, Chongqing (CN); Yijun Jia, Chongqing (CN); Zhao Ye, Chongqing (CN); Haoyang Yang, Chongqing (CN); Renqing Jiang, Chongqing (CN)

(73) Assignee: Army Medical University, Chongqing (CN)

( * ) Notice: Subject to any disclaimer, the term of this patent is extended or adjusted under 35 U.S.C. 154(b) by 350 days.

(21) Appl. No.: 17/979,983

(22) Filed: Nov. 3, 2022

(65) Prior Publication Data

US 2023/0218168 A1    Jul. 13, 2023

(30) Foreign Application Priority Data

Dec. 7, 2021  (CN) .......................... 202111483531.7

(51) Int. Cl.
*G16H 40/20*    (2018.01)
*G06V 20/00*    (2022.01)
(Continued)

(52) U.S. Cl.
CPC ............. *G16H 40/20* (2018.01); *G06V 20/17* (2022.01); *G06V 20/38* (2022.01); *G06V 40/103* (2022.01);
(Continued)

(58) Field of Classification Search
CPC ........ G16H 50/20; G16H 50/80; G16H 30/40; G06V 20/17; G06V 40/16; G06V 40/103; G06V 20/38
See application file for complete search history.

(56) References Cited

U.S. PATENT DOCUMENTS

| 11,881,315 B1* | 1/2024 | Soon-Shiong | ......... G16H 50/30 |
| 11,954,862 B2* | 4/2024 | Ren | ........................ G16H 30/40 |

(Continued)

*Primary Examiner* — David Bilodeau
(74) *Attorney, Agent, or Firm* — Occhiuti & Rohlicek LLP (57) ABSTRACT

Provided is an intelligent system for search and rescue in a special environment such as a disaster, including a body surface feature extracting apparatus, a vital sign extracting apparatus, a speech feature extracting apparatus and a network transmission apparatus that are successively in communication connection with one another. The body surface feature extracting apparatus uses a gated recurrent unit (GRU) network model for transmission and storage. The speech feature extracting apparatus includes a sound collecting module, a sound feature extracting module and a sound analyzing and processing module that are successively in communication connection with one another, with the sound analyzing and processing module being provided with a noise database comprising a plurality of ambient sounds. The network transmission apparatus includes a Zigbee network communication module, a network transmission module, a drone network relay module and a network receiving base station that are successively in communication connection with one another.

8 Claims, 7 Drawing Sheets

(51) Int. Cl.
*G06V 20/17* (2022.01)
*G06V 40/10* (2022.01)
*G06V 40/16* (2022.01)
*G16H 30/40* (2018.01)
*G16H 50/20* (2018.01)
*G16H 50/80* (2018.01)

(52) U.S. Cl.
CPC ............. *G06V 40/16* (2022.01); *G16H 30/40* (2018.01); *G16H 50/20* (2018.01); *G16H 50/80* (2018.01); *Y02D 30/70* (2020.08)

(56) References Cited

U.S. PATENT DOCUMENTS

| | | | |
|---|---|---|---|
| 2008/0207115 A1* | 8/2008 | Lee | H04L 67/52 455/3.06 |
| 2020/0375825 A1* | 12/2020 | Gerstner | A61F 17/00 |
| 2022/0070247 A1* | 3/2022 | Wang | H04L 67/75 |
| 2022/0262263 A1* | 8/2022 | Elhossini | G06V 10/751 |
| 2023/0014243 A1* | 1/2023 | Sequeira | G01S 13/888 |

* cited by examiner

FIG. 11

INTELLIGENT SYSTEM FOR SEARCH AND RESCUE IN SPECIAL ENVIRONMENT SUCH AS DISASTER

CROSS REFERENCE TO RELATED APPLICATION

This patent application claims the benefit and priority of Chinese Patent Application No. 202111483531.7, filed on Dec. 7, 2021, the disclosure of which is incorporated by reference herein in its entirety as part of the present application.

TECHNICAL FIELD

The present disclosure relates to the technical field of logistical support, particularly to an intelligent system for search and rescue in a special environment such as a disaster, and more particularly to a device and method for extracting multiple features of an injured person in a complex environment.

BACKGROUND

Mass rescue operations need to be conducted to rescue stranded people and protect the life and property safety after geological disasters such as an earthquake and mountain landslide occur. There are also potential safety hazards for workers who participate in the mass rescue operations because the persistent occurrence of emergencies such as aftershocks after the occurrence of an earthquake and surface collapse after mountain landslide may cause new accidents. If no necessary measure is taken, the rescue workers may become new victims.

As a matter of course, the in-service rescue workers may have received necessary safety training, but may also be helplessness in the face of great disasters. Especially in a high mountain region, after an earthquake occurs, it may cause communication outage, traffic stop, and signal attenuation. Consequently, people are trapped, and it is very hard to acquire and convey the information of injured people on the scene, leading to extraordinary difficulties in search and rescue of injured people, allocation and planning of relief supplies and medical personnel, selection of rescue plans and the like in the process of on-scene emergency rescue.

In view of the above-mentioned problems, there is an urgent need to provide rescue workers with an intelligent system for on-scene emergency rescue that can intelligently acquire natural and injury feature information of a rescue scene, such as landform, states of injuries, the number of injured people, and the distribution of people in related areas, and also can intelligently perform denoising and accurately transmit information. Moreover, the system further can reduce the capacity of features to achieve rapid and efficient transmission. Meanwhile, the system can make intelligent decisions after effectively acquiring such information to automatically match the required rescue materials, the number of rescued people and the number of people in participating in the rescue, and plan search and rescue routes and evacuation routes for selection. Such a system is significantly helpful for improving the efficiency and quality of rescue and crucial to the reduction of the mortality rate of the injured people.

SUMMARY

An object of the present disclosure is to provide an intelligent system for search and rescue in a special environment such as a disaster, which can restore a disaster scene, construct a communication network, accurately acquire and intelligently form a rescue solution to solve the problem of ineffective rescue under the conditions of weak signal, traffic stop and difficult injury condition acquisition in the disaster scene in the prior art.

The present disclosure is implemented according to the following technical solution.

An intelligent system for search and rescue in a special environment such as a disaster includes a body surface feature extracting apparatus, a vital sign extracting apparatus, a speech feature extracting apparatus and a network transmission apparatus that are successively in communication connection with one another, where the body surface feature extracting apparatus includes a memory that stores a computer program, and a controller that is configured to read the computer program and perform the following operations: acquiring at least one image, with each of the at least one image including at least one object to be identified; convolving and pooling each of the at least one image, and then inputting each convolved and pooled image to a trained gated recurrent unit network model to extract features from each of the at least one object to be identified;

the vital sign extracting apparatus includes a vital sign collecting module configured to acquire information of a blood pressure, a blood oxygen saturation degree, a body temperature, a respiratory rate and a heart rate, and a global positioning system (GPS) or Beidou injured person positioning module provided with a positioning chip for acquiring a position of an injured person;

the speech feature extracting apparatus includes a sound collecting module, a sound feature extracting module and a sound analyzing and processing module that are successively in communication connection with one another, with the sound analyzing and processing module being provided with a noise database including a plurality of ambient sounds and configured to perform denoising by eliminating the ambient sounds in the noise database through wavelet analysis; and the network transmission apparatus includes a Zigbee network communication module, a network transmission module, a drone network relay module and a network receiving base station that are successively in communication connection with one another, with the Zigbee network communication module being configured to transmit information of body surface features, vital signs, sounds and positions, the network transmission module configured to automatically search for and send information to a relay network, the drone network relay module configured to receive data and send the data to a receiving network, and the network receiving base station configured to receive data and transmit the data to a server.

Further, the body surface feature extracting apparatus further includes an image capturing device configured to capture an image of a body surface morphology.

Further, the gated recurrent unit network model includes at least one gated recurrent unit; each of the at least one gated recurrent unit includes a candidate hidden layer for calculating input information thereto based on an ordinary differential equation to convert the input information into a sequence of hidden states for outputting.

Further, the candidate hidden layer calculates the input information thereto by using Euler method or Runge-Kutta to convert the input information into a sequence of hidden states for outputting.

Further, the intelligent system for search and rescue in a special environment such as a disaster includes a feature coding unit that includes a feature database configured to store feature information and a feature coding module configured to code and transmit medical description of a feature.

Further, the feature coding unit follows the following coding rule:
- S1, using 15 digits, including three major indicators: an anatomic subarea, a physiological indicator, and a laboratory indicator, which are each represented by 5 digits and spaced apart by commas;
- S2, coding of the anatomic subarea: including 5 digits, where the first digit represents a large anatomic site, coded as 1 to 8; the second and third digits represent injury location; and the fourth and fifth digits represent an injury type;
- S3, coding of the physiological indicator: including 5 digits, where the first to fifth digits represent a heart rate, a systolic pressure, a body temperature, a respiratory rate and a glosgow coma score, respectively; and
- S4, coding of the laboratory indicator: including 5 digits, where the first to fifth digits represent a hemoglobin concentration, a base excess, an international normalized ratio (JNR), a blood platelet count and a fibrinogen concentration, respectively.

Further, the intelligent system for search and rescue in a special environment such as a disaster also includes an analyzing unit that includes a body surface feature analyzing module configured to analyze vital sign data and obtain an injury severity grade, an injury code decoding module configured to decode a compressed injury code for conversion into an injury condition of an injured person, and a medical resource allocating module configured to form an allocation plan of relief supplies and medical personnel required by the injured person.

Further, the intelligent system for search and rescue in a special environment such as a disaster also includes a disaster scene simulating unit that includes a geographic information system (GIS) mapping module configured to automatically generate a three-dimensional (3D) topographic map of a disaster scene from a satellite map and a contour map of the disaster scene, an injured person positioning module configured to place a mark of collected position information of an injured person on the 3D topographic map, a rescue route planning module configured to plan a route of search and rescue and evacuation for the injured person, and a visualizing module configured to synchronously display the 3D topographic map of the disaster scene, the position of the injured person, the route of search and rescue and evacuation, and the allocation plan of relief supplies and medical personnel on a computer terminal display.

Compared with the prior art, the present disclosure has the following advantages and beneficial effects:

1. The body surface features of an injured person are accurately extracted by the body surface feature extracting apparatus, and stored and transmitted by the gated recurrent unit network model. The candidate hidden layer of the gated recurrent unit network model uses the ordinary differential equation, takes the derivatives of hidden states as parameters and changes the existing discrete values of the parameters into continuous values. During training, the parameters do not need to be orderly transferred to each function in forward propagation to be evaluated. Thus, there is no need to use a lot of space to store intermediate results. In this way, the storage space is greatly reduced, and the memory efficiency is improved. The storage space can be reduced and the transmission efficiency can be improved.

2. The ambient speech information of the disaster scene is extracted by the speech feature extracting apparatus, and the noise database including a plurality of ambient sounds is established. The ambient sounds in the noise database are denoised by wavelet analysis to obtain the real voice of an injured person for accurate analysis.

3. A communication network for injured people and logistical support personnel is constructed by the network transmission module, the drone network relay module and the network receiving base station to guarantee accurate transmission of information of the disaster scene. Moreover, with three nodes, Zigbee is capable of starting, sending and receiving autonomously and thus enabled to have the characteristics of low cost, low rate, low time delay, high capacity and high safety. The communication is realized for the disaster scene so that the information of the injured people can be transmitted.

4. The drone network relay module transmits a relay signal with a drone as a carrier. Thus, the problems of wide scattering range and flexible and changing positions of the injured people in the disaster scene are solved, and the defect of a fixed coverage area of a traditional fixed signal tower is overcome.

5. Furthermore, a special coding form is adopted, thereby reducing the transmission capacity and helping carry out high-speed accurate injury condition transmission. Meanwhile, the combination of the physiological indicators and the laboratory indicators can guide rapid medical rescue decision making, helping reduce the risks of injuries and deaths.

In short, according to the present disclosure, a well-developed rescue system is formed based on the accurate extraction of multiple features, the construction and rapid transmission of a local network, and the automatic generation of a rescue solution. The real conditions of the disaster scene are restored and intelligent rescue is realized. The problems of weak signal, traffic stop and difficult injury condition acquisition in the disaster scene are effectively solved. This system provides basis for accurately carrying out rescue operations and helps reduce the mortality rate of the rescue workers.

BRIEF DESCRIPTION OF THE DRAWINGS

The drawings described herein are provided for further understanding on the embodiments of the present disclosure, and constitute a part of the present application rather than a limit to the embodiments of the present disclosure.

DETAILED DESCRIPTION OF THE EMBODIMENTS

The present disclosure will be further described below with reference to the accompanying drawings and specific embodiments. It should be noted here that the description of these embodiments is intended to help understand the present disclosure rather than limit the present disclosure. The specific structural and functional details disclosed herein are only intended to describe exemplary embodiments of the present disclosure. However, the present disclosure may be embodied in many alternative forms, but it does not mean that the present disclosure is limited to the embodiments set forth herein.

It should be understood that although the terms such as "first" and "second" may be used herein to describe different units, these units are not limited by these terms. These terms are only used to distinguish one unit from another. For example, a first unit may be referred to as a second unit, and a second unit may be referred to as a first unit similarly, without departing from the scope of the exemplary embodiments of the present disclosure.

It should be understood that the term "and/or" used herein only refers to an association relationship for describing associated objects and represents that there may be three relationships. For example, A and/or B may represent the following three cases: there is A alone; there is B alone; and there are both A and B. The term "/and" used herein refers to another relationship between associated objects and represents that there may be two relationships. For example, A/and B may represent the following two cases: there is A alone, and there are both A and B. In addition, the character "/" used herein generally indicates an "or" relationship between the associated objects before and after the character.

It should be understood that specific details are provided in the following description to provide a full understanding of the exemplary embodiments. However, those of ordinary skill in the art will understand that the exemplary embodiments can be implemented without these specific details. For example, the system may be shown in a block diagram to avoid the use of unnecessary details to obscure an example. In other examples, well-known procedures, structures and techniques may not be shown in unnecessary details to avoid making the exemplary embodiments unclear.

Figure 1:
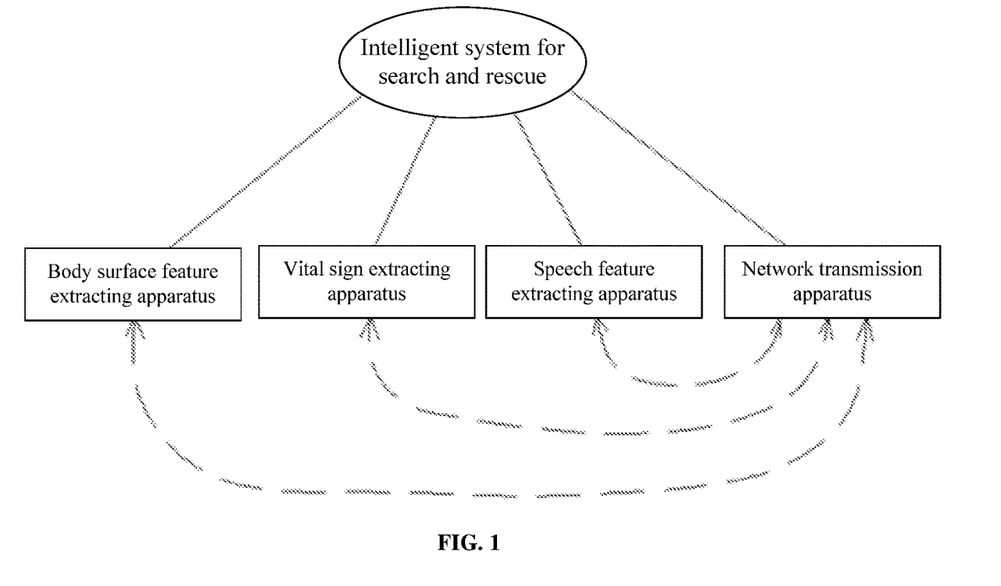
FIG. 1 is a schematic diagram of a structure according to the present disclosure.

As shown in FIG. 1, the present disclosure provides an intelligent system for search and rescue in a special environment such as a disaster, including a body surface feature extracting apparatus, a vital sign extracting apparatus, a speech feature extracting apparatus and a network transmission apparatus that are successively in communication connection with one another. The body surface feature extracting apparatus is configured to acquire information such as body surface features. The vital sign extracting apparatus is configured to the information of vital signs. The speech feature extracting apparatus is configured to acquire voice information of an injured person. The network transmission apparatus is configured to transmit such information.

Figure 2:
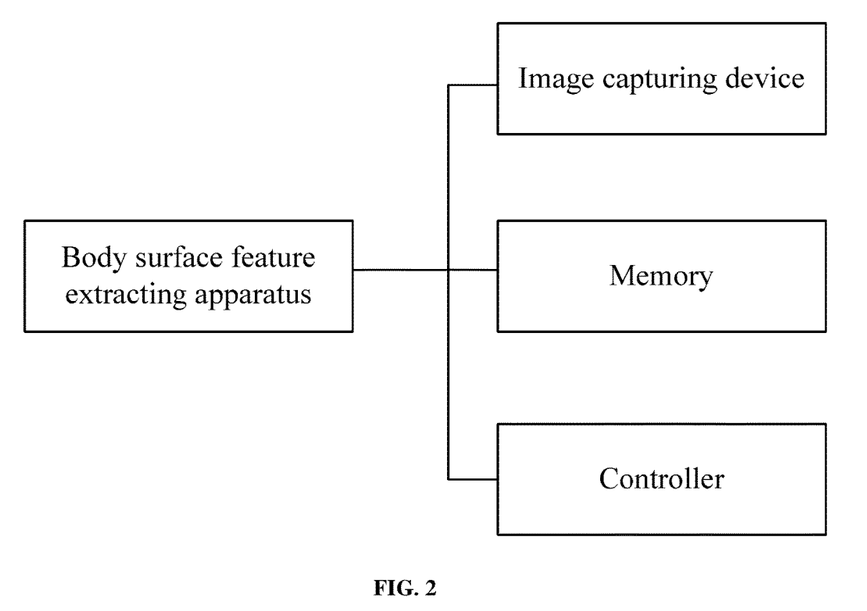
FIG. 2 is a schematic diagram of a structure of a body surface feature extracting apparatus.
Figure 3:
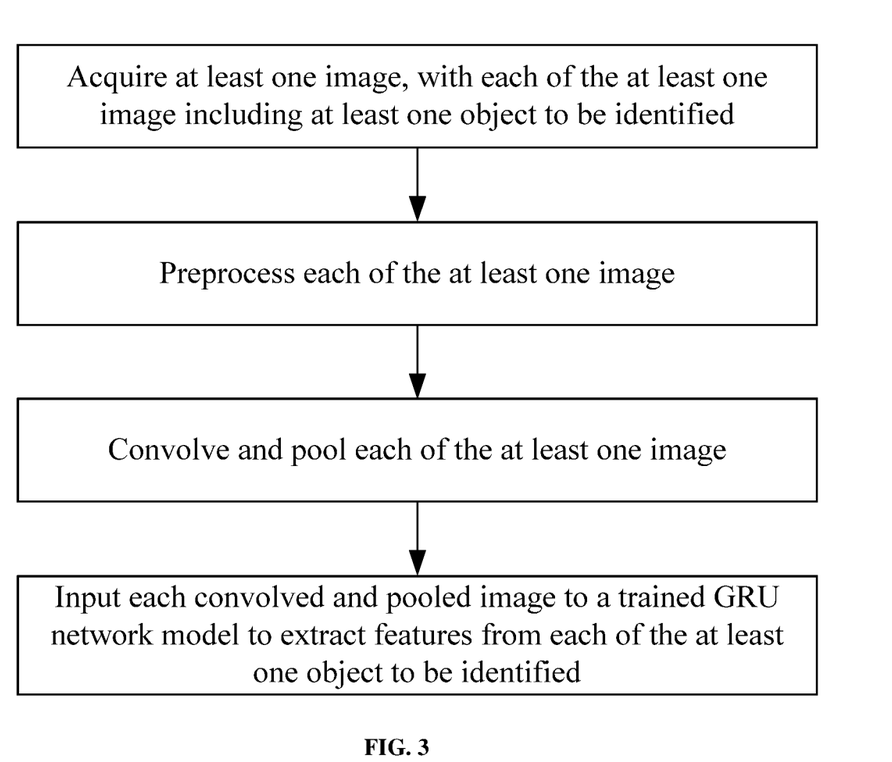
FIG. 3 is a flowchart of a body surface feature extracting method.

As shown in FIG. 2, the body surface feature extracting apparatus in this embodiment includes an image capturing device, a memory and a controller. The memory is in communication connection with the controller and capable of information transmission. The memory stores a computer program. The controller is configured to read the computer program and control the image capturing device to acquire a surface morphology image. When acquiring an image, as shown in FIG. 3, the specific steps are as follows:

Step S01, at least one image is acquired, with each of the at least one image including at least one object to be identified.

The image may be an image acquired in real time or an image stored on the cloud or a locally stored image, which is not limited here. The image capturing device may be based on an ordinary camera, a video camera or a red, green, blue-depth (RGB-D) camera. Preferably, the RGB-D camera is used to acquire an RGB-D image including an RGB image and a depth image. Azure Kinect DK of the RGB-D camera captures the depth image containing an object to be identified. The Azure Kinect DK carries a 1 mega pixel advanced depth camera, a 360-degree microphone array, a 12 mega pixel full high-definition camera and a direction sensor and is applicable to advanced computer vision and speech model development. In this step, to identify an injury type, the image should contain an injury to be identified. To identify a human face, the image should contain a human face to be identified. For other applications, the image should similarly contain the corresponding objects to be identified. More preferably, the RGB-D camera is fixed on the body of an injured person and capable of capturing an image of a body surface morphology, for example, information such as shapes of limbs, facial state and injury of the injured person, at a near distance. As a matter of course, the camera may be also fixed to a drone and moved together with the flying of the drone to perform near-distance imaging. Thus, the workload of near-distance observation by a person can be avoided.

Step S02, each of the at least one image is preprocessed.

Specifically, a preprocessing method used in this solution is as follows: noise points are removed by filling in holes of each of the at least one image using a bilateral filtering algorithm so that the depth image is clearer. Bilateral filtering, composed of two Gaussian kernel functions, overcomes the drawbacks of Gaussian filtering by means of non-linear combination of the space domain information and the gray domain information of the depth image, and takes into account the edge information of the image during depth inpainting so that the image edge is clearer and smoother than that obtained by Gaussian filtering.

The bilateral filtering is defined as:

$$F(m, n) = \frac{\sum_{(i,j)\in\Omega} \omega_s(i, j)\omega_r(i, j)f(i, j)}{\beta},$$

$$\beta = \sum_{(i,j)\in\Omega} \omega_s(i, j)\omega_r(i, j),$$

$$\omega_s(i, j) = \exp\left[-\frac{(i-m)^2 + (j-n)^2}{2\sigma_s^2}\right],$$

$$\omega_r(i, j) = \exp\left\{-\frac{[f(i, j) - f(m, n)]^2}{2\sigma_r^2}\right\},$$

$$\omega = \omega_s \times \omega_r,$$

where $\omega_s$ represents a filtering kernel of a space domain; (i,j) represents the position of a current point; (m, n)

represents the middle position of the filtering kernel; $\sigma_s$ represents the standard deviation of the space domain; $\omega_r$ represents a filtering kernel of a pixel domain; f (i,j) represents the gray value of a current traversal point; f (m, n) represents the gray value of a middle position of the filtering kernel; $\sigma_r$ represents the standard deviation of the pixel domain; and $\beta$ represents a sum of products of $\omega_s$ and $\omega_r$ after the traversal of convolution kernels.

w represents a filtering kernel. F(m,n) represents the gray value of the center point of the filtering kernel. $\Omega$ represents the space of the image; and i and j belong to $\Omega$, indicating points in the image, with i representing the x-coordinate of a traversal point and j representing the y-coordinate of the traversal point. m represents the x-coordinate of the center point of the filtering kernel, and n represents the y-coordinate of the center point of the filtering kernel.

Step S03, each of the at least one image is convolved and pooled. By convolving, brighter pixels in an output image may represent the edge present in an injury image so that the edge information of the injury image is obtained. By pooling, the robustness of the network is enhanced, and a certain anti-disturbance effect is achieved. Specifically, each of the at least one image may be convolved and pooled using a convolutional neural network.

Step S04, each convolved and pooled image is input to a trained gated recurrent unit (GRU) network model to extract features from each of the at least one object to be identified, where the GRU network model is one based on an ordinary differential equation.

In this step, the GRU network model needs to be trained in advance, and different training sets are used according to different objects to be identified.

With the extracted features, the object to be identified may be further classified and identified, such as the depth, size and bleeding condition of an injury, gunshot injury or scratch, to further drive a back-end intelligent device, e.g., a back-end processing unit in this embodiment.

The GRU network model based on the ordinary differential equation in this method parameterizes hidden states into a continuous function of time. Parameters of the neighboring "network layer" are linked together automatically, thereby reducing the number of parameters required for supervising a learning task, saving the training time of the network and guaranteeing the stability of the model. The whole method is based on the RGB-D image, integrally utilizes the color and depth information, and uses a multi-data pattern feature extraction strategy to identify an RGB-D object.

Figure 4:
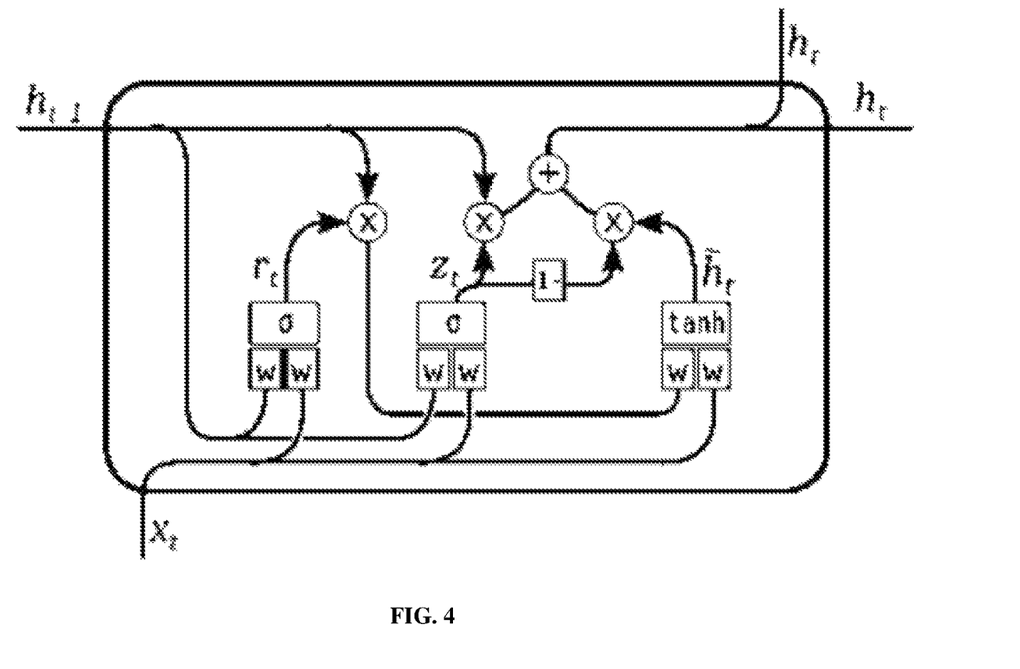
FIG. 4 is an architecture diagram of a gated recurrent unit.

The GRU network model based on the ordinary differential equation described above includes at least one gated recurrent unit. When there are a plurality of gated recurrent units, the plurality of gated recurrent units are connected to one another in series.

The gated recurrent unit includes a reset gate $r_t$, an update gate $z_t$ and a candidate hidden layer $\tilde{h}_t$. The linkage of the reset gate $r_t$, the update gate $z_t$ and the candidate hidden layer $\tilde{h}_t$ is the prior art, as shown in FIG. 4, which will not be redundantly described here. The reset gate $r_t$, the update gate $z_t$ and the candidate hidden layer $\tilde{h}_t$ each use the state information $h_{t-1}$ of a previous time point and original data as inputs. In this solution, the candidate hidden layer $\tilde{h}_t$ of each gated recurrent unit calculates the input information thereto based on the ordinary differential equation and converts it into a sequence of hidden states for outputting.

The gated recurrent unit takes the form of a structure similar to an existing GRU. The hidden state is calculated from a functional derivative of the hidden state between observed values. The GRU network model is continuous. The desired sequence of hidden states may be obtained by solving the ordinary differential equation. During each evaluation, the equation is solved starting from initial state $h_0$.

The GRU network model mainly utilizes the ordinary differential equation to calculate the output ht of the gated recurrent unit. Specifically, the ordinary differential equation may use Euler method or Runge-Kutta method. The model uses function odeRNNCell to calculate the change or derivative of the hidden state at time t. As shown by the following formula, odeRNNCell is a common initial value problem, which depends on the values of initial observed value $y_0$ and hidden state $h_0$ at time $t_0$.

$y_1$=ODESOLVER(odeRNNCell,tuple($y_0$,$h_0$),t).

where ODESOLVER is an ordinary differential solver, and odeRUNCell is an ordinary differential recursive neuron function.

Update functions for the reset gate $r_t$, the update gate $z_t$, the candidate hidden layer $\tilde{h}_t$ and an output gate $o_t$ are expressed respectively as follows:

$$r_t = \sigma(W_r x_t + U_r h_{t-1} + b_r)$$

$$z_t = \sigma(W_z x_t + U_z h_{t-1} + b_r)$$

$$\tilde{h}_t = \tanh(W_r x_t + U_r r_t + b_r)$$

$$o_t = \sigma(W_o h_t + b_0)$$

where t is a time series; $W_r$ is a link weight of the current input in the reset gate; $U_r$ is a link weight of the previous layer in the reset gate; $W_z$ is a link weight of the current input in the update gate; $U_z$ is a link weight of the previous layer in the update gate; $W_o$ is a link weight of the output; $b_r$ is a deviation parameter of the reset gate; and $b_o$ is a deviation parameter of the output.

The method is as follows:

An initial value and the initial value of the hidden layer are firstly substituted into x and h, $x \leftarrow$ states[0]

$h \leftarrow$ states[1]

The parameters of the GRU network model are derived and updated by the above update functions, $r_t, z_t, \tilde{h}_t \leftarrow$ updatedGRU Function(x,h,parameters)

A gradient of the corresponding ht is derived according to the architecture of the GRU network model, $h_t \leftarrow \tilde{h}_t (1 - z_t)$ $o_t \leftarrow \sigma(W_o h_t + b_o)$ return $do_t/dt$, $dh_t/dt$.

This gradient value may be used to verify whether the code of the calculated neural network values is correct. A neural network model having numerous layers may have the problems of gradient vanishing and gradient explosion during training so that the whole network cannot operate normally. By verification using the gradient value, the accuracy of the construction of the neural network is further improved.

The candidate hidden layer of the GRU network model uses the ordinary differential equation, takes the derivatives of the hidden states as parameters and changes the existing discrete values of the parameters into continuous values.

During training, the parameters do not need to be orderly transferred to each function in forward propagation to be evaluated. Thus, there is no need to use a lot of space to store intermediate results. In this way, the storage space is greatly reduced, and the memory efficiency is improved. The storage space can be reduced and the transmission efficiency can be improved.

Figure 5:
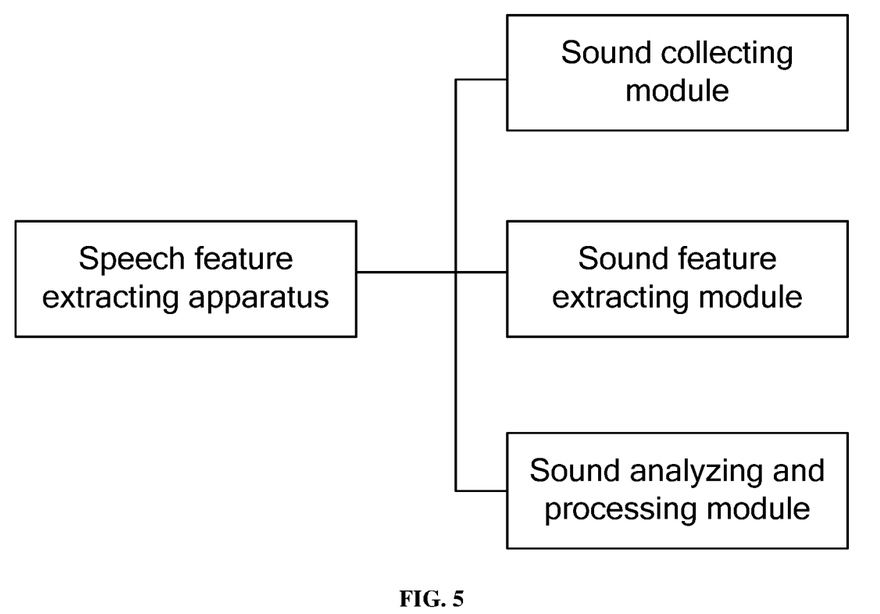
FIG. 5 is a schematic diagram of a structure of a speech feature extracting apparatus.

As shown in FIG. 5, the speech feature extracting apparatus includes a sound collecting module, a sound feature extracting module and a sound analyzing and processing module that are successively in communication connection with one another.

The sound collecting module is ATK-VS1053MP3 module developed by ALIENTEK. The frequency and the effective range of the sound extracted are as follows: 20 HZ to 20 KHZ, and 0 to 190 db. The sound frequency and decibel requirements of a disaster scene are met, and effective extraction can be achieved. A sound signal can be generated directly and conveniently, and the magnitude of the sound signal may reflect the intensity of the change of the surrounding to a certain extent. In the process of movement of a normal person, a breath air flow passes through the respiratory tract and the pulmonary alveoli to generate a turbulent flow and induce vibration, thereby making a sound. The sound transmitting to the body surface through the lung tissue and the chest wall is breath sound. In the process of movement of each person, different breath sounds may be generated due to different physical states, and therefore, the breath sound of a person in the process of movement may be analyzed to determine the physical state of the person.

The sound feature extracting module is an independently developed structure. The core of the sound feature extracting module is a denoising algorithm, and the principle thereof is denoising and filtering the sound collected by the sound collecting module to obtain effective sound information to be processed. A denoising method used is as follows: various ambient sounds are simulated previously to form a noise database, which is combined with wavelet analysis to realize denoising. A self-learning algorithm is used later to enrich the noise database.

The sound analyzing and processing module is speech digital signal processor (DSP) chip FM1188 which performs dimensionality reduction algorithm processing on initial feature parameters of all frames of a sound sample using Fisher dimensionality reduction method to obtain a feature vector of the sound sample. The feature vector of the sound sample of the injured is used to train the neural network model, and the sound sample is compared with normal body sound information. If the resulting evaluation score is higher than a set value, the physical state of the injured person is reported through a narrow-band Internet-of-Things module.

Figure 6:
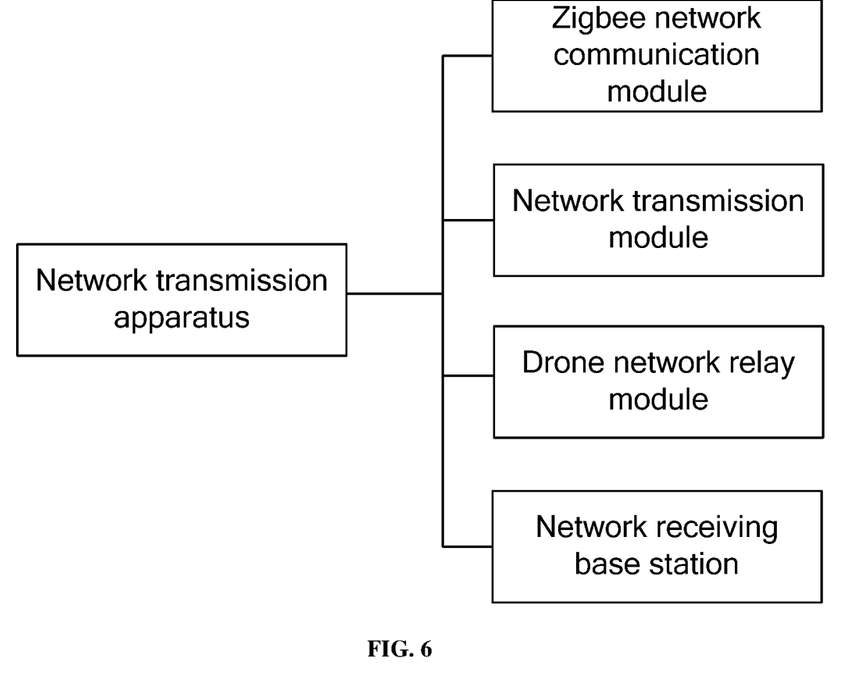
FIG. 6 is a schematic diagram of a structure of a network transmission apparatus.

As shown in FIG. 6, the network transmission apparatus includes a Zigbee network communication module, a network transmission module, a drone network relay module and a network receiving base station that are successively in communication connection with one another. The Zigbee network communication module is fixed on the body of an injured person and configured to transmit information of body surface features, vital signs, sound and position. The network transmission module is fixed on the body of the injured person and configured to automatically search for and send information to a relay network. The drone network relay module is fixed on the body of the injured person and capable of moving within a certain range to receive data from the relay network and send the data to a receiving network. The network receiving base station is configured to receive data and transmit the data to a server.

Figure 11:
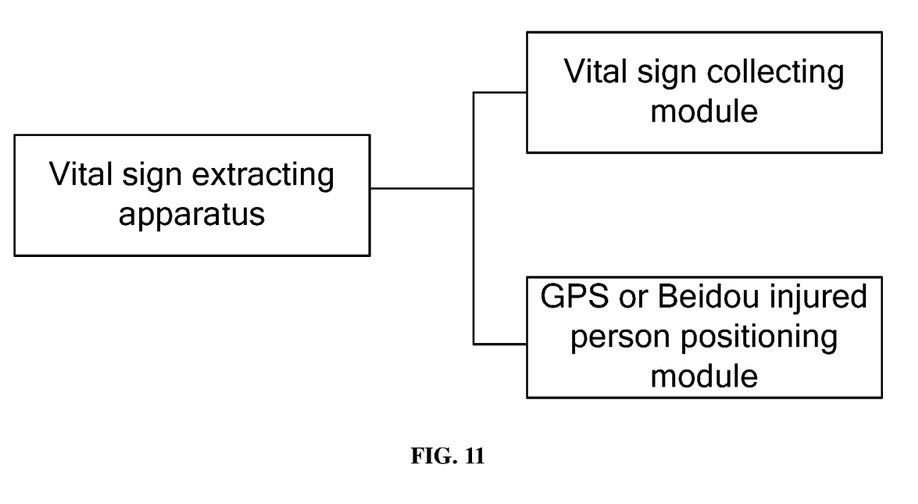
FIG. 11 is a schematic diagram of a structure of a vital sign extracting apparatus.

As an improvement of this embodiment, as shown in FIG. 11, the vital sign extracting apparatus includes a vital sign collecting module and a global positioning system (GPS) or Beidou injured person positioning module. The vital sign collecting module is fixed on the body of an injured person and configured to acquire vital sign information of a blood pressure, a blood oxygen saturation degree, a body temperature, a respiratory rate, a heart rate and the like through different sensors. The GPS or Beidou injured person positioning module is provided with a positioning chip for acquiring a position of an injured person to acquire and receive information at a near distance.

As a matter of course, the GPS or Beidou injured person positioning module may also cooperate with the body surface feature extracting apparatus to acquire, receive and transmit body surface information.

Figure 9:
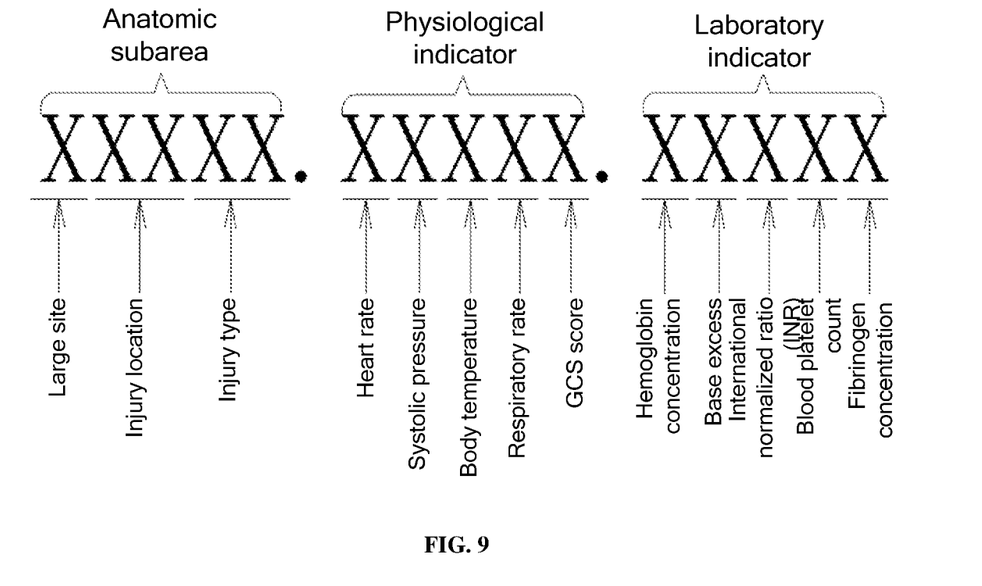
FIG. 9 is a diagram showing a coding rule of a feature coding unit according to the present disclosure.

As a further improvement of this embodiment, the system further includes a feature coding unit. The feature coding unit includes a feature database configured to store feature information, such as an injury position, an injury type and an injury depth, and a feature coding module configured to code and transmit the medical description of a feature, thereby reducing the load of speech to the network during transmission.

As shown in FIG. 9, the feature coding unit follows the following coding rule:

1, three major indicators, namely an anatomic subarea, a physiological indicator, and a laboratory indicator, are included, which are each represented by 5 digits and spaced apart by commas.

2, coding of the anatomic subarea: 5 digits are included. The first digit represents a large anatomic site, including head, maxillofacial region, neck, chest, abdomen, pelvis, limbs and others, respectively coded as 1 to 8. The second and third digits represent injury location. An injury is located according to the characteristics of each anatomic subarea, and injury location is not necessarily the same between anatomic subareas. The fourth and fifth digits represent an injury type. The injury type in each anatomic site is different, and an injury may be classified according to the major injury characteristics of each anatomic site. The second and third digits and the fourth and fifth digits may be increased according to an actual injury condition.

When a plurality of injuries are caused or a plurality of sites have injuries, the anatomic sites are connected by "+". Injuries in the same anatomic site are connected by "−".

3, coding of the physiological indicator: 5 digits are included. The first to fifth digits represent a heart rate, a systolic pressure, a body temperature, a respiratory rate and a glasgow coma score, respectively.

4, coding of the laboratory indicator: 5 digits are included. The first to fifth digits represent a hemoglobin concentration, a base excess, an international normalized ratio (INR), a blood platelet count and a fibrinogen concentration, respectively.

During coding of the above-mentioned indicators, a digit within the range of from 1 to 10 is used to represent an interval. For example, 1 represents that the systolic pressure is 90-140 mmHg; 2 represents that the systolic pressure is 60-89 mmHg, and so on. Thus, the storage content is smaller, which is conducive to the transmission quantity.

A significant advantage of the above-mentioned coding mode is that the storage content is greatly reduced, facilitating remote transmission, especially in case of poor communication signals in wartime. An injury condition may be reflected bilaterally and accurately.

Another significant advantage of the above-mentioned coding mode is that the physiological indicator and the laboratory indicator may be used to guide anabiosis and the selection of a surgical way. Thus, a surgery can be conducted immediately, thereby reducing casualties.

Figure 7:
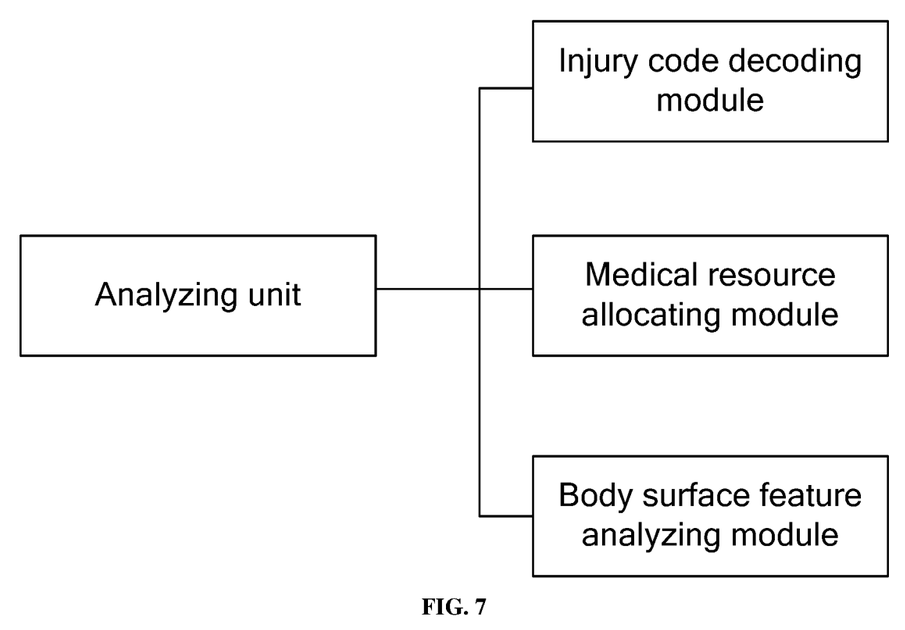
FIG. 7 is a schematic diagram of a structure of an analyzing unit.

As shown in FIG. 7, as a further improvement of this embodiment, the system further includes an analyzing unit. The analyzing unit includes a body surface feature analyzing module configured to aggregate the data of vital signs, body surface features and speech features of an injured person and calculate an injury severity grade of the injured person by an algorithm, an injury code decoding module configured to decode an injury code for conversion into an injury condition of an injured person, and a medical resource allocating module configured to automatically calculate an allocation plan of relief supplies and medical personnel required by the injured person by an algorithm based on the injury severity grade and the injury condition of the injured person.

The analyzing unit analyzes and processes the feature information to obtain a reasonable implementation plant, and a perfect intelligent decision making process is formed actually.

Figure 8:
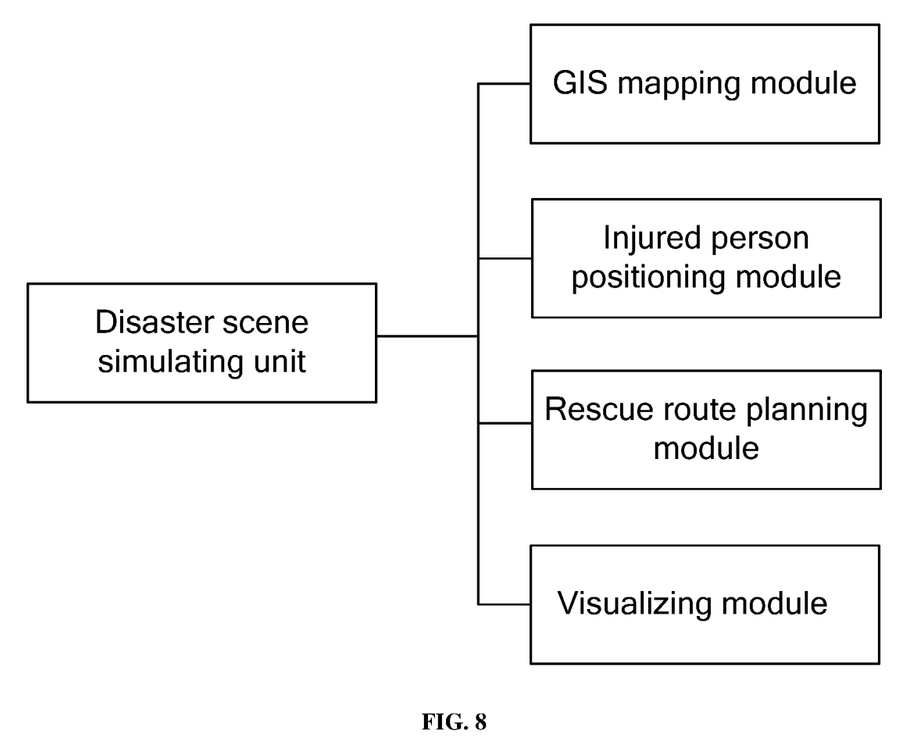
FIG. 8 is a schematic diagram of a structure of a disaster scene simulating unit.

As shown in FIG. 8, as a further improvement of this embodiment, the system further includes a disaster scene simulating unit. The disaster scene simulating unit includes a geographic information system (GIS) mapping module configured to automatically generate a three-dimensional (3D) topographic map of a disaster scene from a satellite map and a contour map of the disaster scene, an injured person positioning module configured to place a mark of collected position information of an injured person on the 3D topographic map, a rescue route planning module configured to automatically plan, for the medical service personnel, a route of search and rescue and evacuation for the injured person by analyzing the landform of the map, and a visualizing module configured to synchronously display the 3D topographic map of the disaster scene, the position of the injured person, the route of search and rescue and evacuation, and the allocation plan of medical resources on a computer terminal display.

Figure 10:
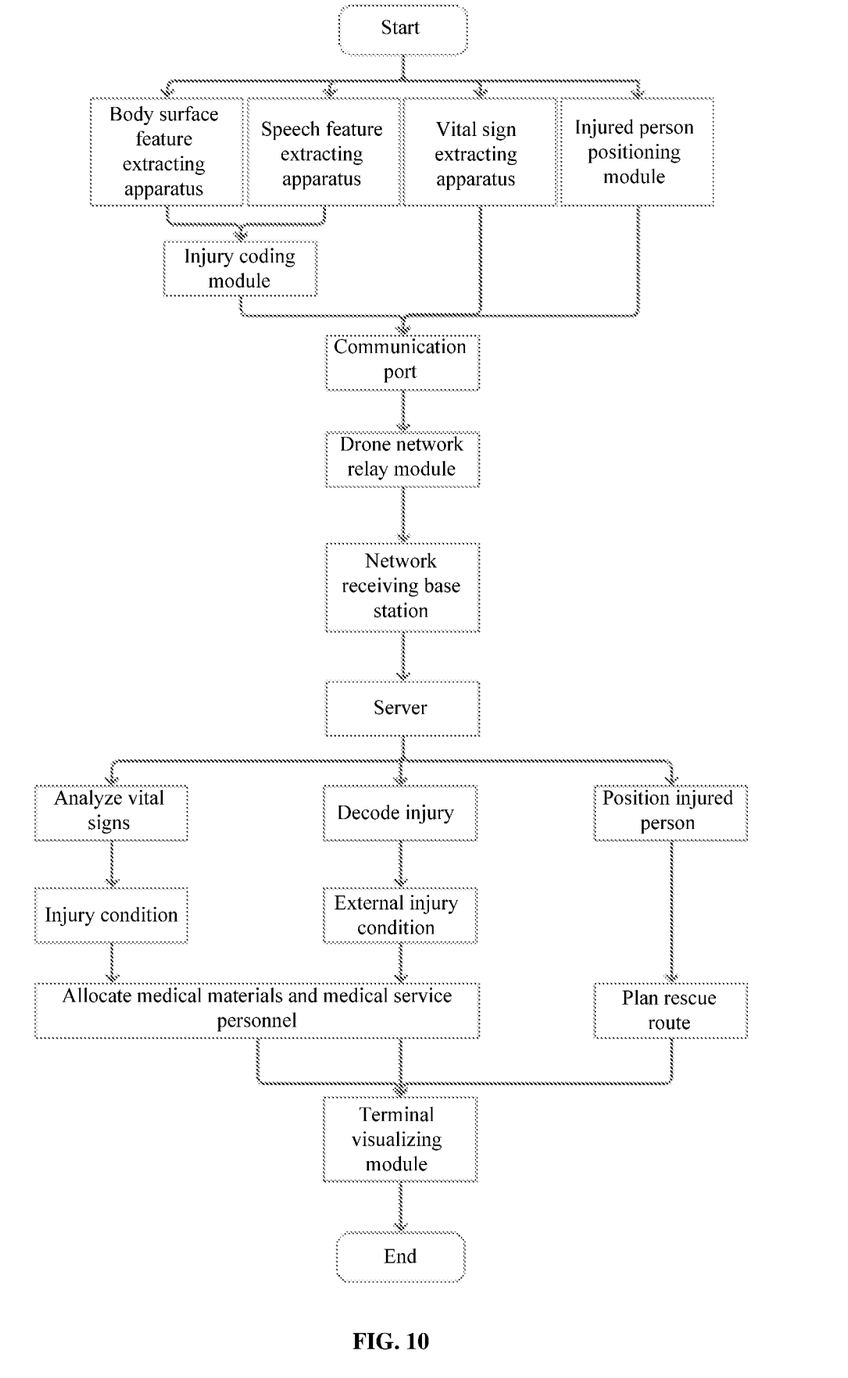
FIG. 10 is a flowchart according to the present disclosure.

When this embodiment is implemented, as shown in FIG. 10, firstly, the information of features such as body surface features and vital signs is collected by the body surface feature extracting apparatus, and sound related feature information is collected by the speech feature extracting apparatus. The medical description of the feature information is then coded by the feature coding unit. The relevant information is remotely transmitted to the analyzing unit by the network transmission apparatus afterwards. The analyzing unit analyzes and processes the relevant information to form the allocation plan of medical resources. Thus, the automatic, rapid decision making process of rescue operations is completed. Moreover, the whole process is reproduced in real time by the disaster scene simulating unit, facilitating decision commanding, especially suitable for decision commanding when the rescue decision making ability is weak or when the scene environment is complicated with a large number of injured people.

The objective, technical solutions and beneficial effects of the present disclosure are further described in detail in the above specific embodiments. It should be understood that the foregoing are merely descriptions of the specific embodiments of the present disclosure and not intended to limit the protection scope of the present disclosure. Any modification, equivalent replacement, improvement, or the like made within the spirit and principle of the present disclosure should fall within the protection scope of the present disclosure.

What is claimed is:

1. An apparatus comprising circuitry for implementing an intelligent system for search and rescue in a special environment such as a disaster, comprising a body surface feature extracting apparatus, a vital sign extracting apparatus, a speech feature extracting apparatus and a network transmission apparatus that are successively in communication connection with one another, wherein the body surface feature extracting apparatus comprises a controller that is configured to cause an image-acquisition circuit to acquire at least one image, with each of the at least one image comprising at least one object to be identified; to cause a convolution circuit to carry out convolving and pooling each of the at least one image, and to then cause each such convolved and pooled image to be input into a trained gated recurrent unit network model to extract features from each of the at least one object to be identified;

wherein the vital sign extracting apparatus comprises a vital sign collecting module configured to acquire information indicative of a blood pressure, a blood oxygen saturation degree, a body temperature, a respiratory rate and a heart rate, and a global positioning system (GPS) or Beidou injured person positioning module provided with a positioning chip for acquiring a position of an injured person;

wherein the speech feature extracting apparatus comprises a sound collecting module, a sound feature extracting module and a sound analyzing and processing module that are successively in communication connection with one another, with the sound analyzing and processing module being provided with a noise database comprising a plurality of ambient sounds and configured to perform denoising by eliminating the ambient sounds in the noise database through wavelet analysis; and wherein the network transmission apparatus comprises a Zigbee network communication module, a network transmission module, a drone network relay module and a network receiving base station that are successively in communication connection with one another, with the Zigbee network communication module being configured to transmit information of body surface features, vital signs, sounds and positions, the network transmission module configured to automatically search for and send information to a relay network, the drone network relay module configured to receive data and send the data to a receiving network, and the network receiving base station configured to receive data and transmit the data to a server.

2. The apparatus of claim 1, wherein the body surface feature extracting apparatus further comprises an image capturing device configured to capture an image of a body surface morphology.

3. The apparatus of claim 1, wherein the gated recurrent unit network model comprises at least one gated recurrent unit; each of the at least one gated recurrent unit comprises a candidate hidden layer for calculating input information thereto based on an ordinary differential equation to convert the input information into a sequence of hidden states for outputting.

4. The apparatus of claim 1, wherein the candidate hidden layer calculates the input information thereto by using Euler method or Runge-Kutta to convert the input information into a sequence of hidden states for outputting.

5. The apparatus of claim 1, wherein the intelligent system for search and rescue in a special environment further comprises a feature coding unit that comprises a feature database configured to store feature information and a feature coding module configured to code and transmit medical description of a feature.

6. The apparatus of claim 5, wherein the feature coding unit follows the following coding rule:
- S1, using 15 digits, comprising three major indicators: an anatomic subarea, a physiological indicator, and a laboratory indicator, which are each represented by 5 digits and spaced apart by commas;
- S2, coding of the anatomic subarea: comprising 5 digits, wherein the first digit represents a large anatomic site, coded as 1 to 8; the second and third digits represent injury location; and the fourth and fifth digits represent an injury type;
- S3, coding of the physiological indicator: comprising 5 digits, wherein the first to fifth digits represent a heart rate, a systolic pressure, a body temperature, a respiratory rate and a glosgow coma score, respectively; and
- S4, coding of the laboratory indicator: comprising 5 digits, wherein the first to fifth digits represent a hemoglobin concentration, a base excess, an international normalized ratio (INR), a blood platelet count and a fibrinogen concentration, respectively.

7. The apparatus of claim 1, wherein the intelligent system further comprises an analyzing unit that comprises a body surface feature analyzing module configured to analyze vital sign data and obtain an injury severity grade, an injury code decoding module configured to decode a compressed injury code for conversion into an injury condition of an injured person, and a medical resource allocating module configured to form an allocation plan of relief supplies and medical personnel required by the injured person.

8. The apparatus of claim 1, wherein the intelligent system further comprises a disaster scene simulating unit that comprises a geographic information system (GIS) mapping module configured to automatically generate a three-dimensional (3D) topographic map of a disaster scene from a satellite map and a contour map of the disaster scene, an injured person positioning module configured to place a mark of collected position information of an injured person on the 3D topographic map, a rescue route planning module configured to plan a route of search and rescue and evacuation for the injured person, and a visualizing module configured to synchronously display the 3D topographic map of the disaster scene, the position of the injured person, the route of search and rescue and evacuation, and the allocation plan of relief supplies and medical personnel on a computer terminal display.

* * * * *